United States Patent
Qiu (10) Patent No.: US 10,966,457 B2
(45) Date of Patent: Apr. 6, 2021

(54) ATOMIZING HEAD, ATOMIZER AND ELECTRONIC CIGARETTE THEREOF

(71) Applicant: CHANGZHOU JWEI INTELLIGENT TECHNOLOGY CO., LTD., Changzhou (CN)

(72) Inventor: Weihua Qiu, Changzhou (CN)

(73) Assignee: CHANGZHOU JWEI INTELLIGENT TECHNOLOGY CO., LTD., Changzhou (CN)

(*) Notice: Subject to any disclaimer, the term of this patent is extended or adjusted under 35 U.S.C. 154(b) by 405 days.

(21) Appl. No.: 16/032,059

(22) Filed: Jul. 10, 2018

(65) Prior Publication Data

US 2018/0317558 A1 Nov. 8, 2018

Related U.S. Application Data

(63) Continuation of application No. PCT/CN2016/113665, filed on Dec. 30, 2016.

(30) Foreign Application Priority Data

Jan. 14, 2016 (CN) .......................... 201610024931.4

(51) Int. Cl.
*A24F 40/485* (2020.01)
*A61M 15/00* (2006.01)
(Continued)

(52) U.S. Cl.
CPC .......... *A24F 40/485* (2020.01); *A24F 47/008* (2013.01); *A61M 11/042* (2014.02);
(Continued)

(58) Field of Classification Search
CPC .................................................... A24F 40/485
See application file for complete search history.

(56) References Cited

U.S. PATENT DOCUMENTS 10,264,820 B2 * 4/2019 Bellinger .............. A24F 47/008
10,667,560 B2 * 6/2020 Atkins ................. A61M 11/042
(Continued)

FOREIGN PATENT DOCUMENTS

CN 2260619 Y 8/1997
CN 1360668 A 7/2002
(Continued)

OTHER PUBLICATIONS

The Chinese Third Examination Report of corresponding China patent application No. 201610024931.4, dated Dec. 18, 2018.
(Continued)

*Primary Examiner* — James Harvey
(74) *Attorney, Agent, or Firm* — J.C. Patents (57) ABSTRACT

Provided are an atomizing head (1), an atomizer (100) and an electronic cigarette. The atomizing head (1) comprises a shell (12) provided with a liquid inlet (121) and an inner cavity (17), and an atomizing head base (81) provided with an air inlet channel (151), where the liquid inlet (121) and the air inlet channel (151) are both in communication with the inner cavity (17); a bottom end of the shell (12) is fixedly connected to the atomizing head base (81); an elastic element (16) encloses an air outlet end of the air inlet channel (151); the elastic element (16) has a first state and a second state; in the first state, the air inlet channel (151) is in communication with the inner cavity (17); and in the second state, the air inlet channel (151) and the inner cavity (17) are blocked up against each other.

10 Claims, 10 Drawing Sheets

(51) Int. Cl.
*A61M 15/06* (2006.01)
*A61M 11/04* (2006.01)
*A24F 47/00* (2020.01)

(52) U.S. Cl.
CPC ........ *A61M 15/0015* (2014.02); *A61M 15/06* (2013.01); *A61M 15/002* (2014.02); *A61M 2205/3653* (2013.01); *A61M 2205/8206* (2013.01)

(56) References Cited

U.S. PATENT DOCUMENTS

| | | | |
|---|---|---|---|
| 10,709,173 B2* | 7/2020 | Monsees | A61M 11/042 |
| 10,736,359 B2* | 8/2020 | Verleur | A24F 40/40 |
| 10,779,573 B2* | 9/2020 | Rose | H05B 3/04 |
| 10,798,973 B2* | 10/2020 | Levitz | A24F 40/90 |
| 2012/0199663 A1* | 8/2012 | Qiu | A61M 15/0081 239/8 |
| 2016/0000147 A1* | 1/2016 | Li | A24F 47/008 131/329 |
| 2018/0317558 A1* | 11/2018 | Qiu | A61M 15/0015 |
| 2019/0209791 A1* | 7/2019 | Courbat | A61M 11/003 |

FOREIGN PATENT DOCUMENTS

| | | |
|---|---|---|
| CN | 101268867 A | 9/2008 |
| CN | 102160906 A | 8/2011 |
| CN | 203467676 U | 3/2014 |
| CN | 203692546 U | 7/2014 |
| CN | 103990207 A | 8/2014 |
| CN | 104126873 A | 11/2014 |
| CN | 204409583 U | 6/2015 |
| CN | 204599324 U | 9/2015 |
| CN | 204796750 U | 11/2015 |
| CN | 105105340 A | 12/2015 |
| CN | 105152371 A | 12/2015 |
| CN | 105192893 A | 12/2015 |
| CN | 204888732 U | 12/2015 |
| CN | 105212278 A | 1/2016 |
| CN | 105476072 A | 4/2016 |
| CN | 205358225 U | 7/2016 |
| JP | 3160708 U | 6/2011 |
| WO | WO 2013/044537 A1 | 4/2013 |

OTHER PUBLICATIONS

The International Search Report of corresponding International PCT Application No. PCT/CN2016/113665, dated Apr. 7, 2017.
The Chinese First Examination Report of corresponding Chinese Application No. 201610024931.4, dated Sep. 15, 2017.
The Chinese Second Examination Report of corresponding Chinese Application No. 201610024931.4, dated May 28, 2018.

* cited by examiner

ATOMIZING HEAD, ATOMIZER AND ELECTRONIC CIGARETTE THEREOF

CROSS-REFERENCE TO RELATED APPLICATIONS

This application is a continuation of International Application No. PCT/CN2016/113665, filed on Jun. 30, 2016, which claims priority to Chinese Patent Application No. 201610024931.4, filed on Jan. 14, 2016. The disclosure of the aforementioned applications is hereby incorporated by reference in their entireties.

TECHNICAL FIELD

The present application relates to the technical field of electronic cigarettes, and in particular, to an atomizing head, an atomizer and an electronic cigarette thereof.

BACKGROUND

An electronic cigarette atomizes liquid tobacco in a cartridge into tobacco, which can be smoked like a traditional cigarette. The existing electronic cigarette generally includes a battery for the electronic cigarette, a control circuit and an atomizer, where the atomizer has an atomizing chamber that is provided with an atomizing head, and the atomizing head includes a liquid absorbing element such as a heating wire, cotton or a cotton cloth, etc. The heating wire is spiral. The spiral heating wire is wrapped with a cotton cloth or cotton outside, and is in communication with a liquid storage cavity through a cotton cloth or cotton, thus introducing tobacco liquid into the heating wire of the atomizing head through osmosis of the cotton or the cotton cloth. In order to achieve the function of smoking, it is also necessary to introduce air to cause the flow of gas flow so as to drive the atomized tobacco into the human body. One or several air inlet holes are generally provided at a lower end of the atomizing chamber, and an insurmountable defect occurs due to the position of the air inlet hole. The air inlet hole is arranged at a lower end of the atomizer, and the liquid absorbing element such as the cotton or the cotton cloth is arranged at an upper part of the air inlet hole. The liquid absorbing element adsorbs the tobacco liquid by osmosis, and when saturation is reached, part of tobacco liquid will exude. Part of the exuded liquid tobacco drops, and will flow out from the air inlet hole when aggregating to a certain degree. Generally, the air inlet hole is non-closable. The impact seeing from the outside is that the tobacco liquid of the electronic cigarette will flow out from the air inlet hole, affecting the cleanliness and use experience.

SUMMARY

In view of the above, in order to overcome the above problems, it is necessary to provide an atomizing head to overcome the problem of liquid leakage from the atomizing head. The present application also provides an atomizer applying the atomizing head and an electronic cigarette applying the atomizer.

The application provides an atomizing head, the atomizing head includes a shell provided with a liquid inlet and an inner cavity, and an atomizing head base provided with an air inlet channel, where the liquid inlet and the air inlet channel are both in communication with the inner cavity; a bottom end of the shell is fixedly connected to the atomizing head base; an elastic element encloses an air outlet end of the air inlet channel; the elastic element has a first state in which the air inlet channel is in communication with the inner cavity and the elastic element also has a second state in which the air inlet channel and the inner cavity are blocked up against each other.

Further, the atomizing head base includes an end portion, a main portion and an air inlet portion, which are arranged in turn from top to bottom; the main portion is provided between the end portion and the air inlet portion, a gap groove is provided between the end portion and the main portion, the end portion and the main portion are provided within the inner cavity, and an end portion of the elastic element is fixed in the gap groove.

Further, the elastic element is provided with an air hole, an air flow through hole serving as the air outlet end of the air inlet channel is provided above the end portion, and the elastic element encloses a periphery of the end portion.

Further, a side wall of the end portion is provided with an air flow through hole serving as the air outlet end of the air inlet channel, and the elastic element is adhered to the side wall of the end portion.

Further, when a portion of the elastic element where the air hole is located moves away from the end portion, the air hole is expanded, and the air hole communicates with the air flow through hole so as to allow the elastic element to be in the first state; when the portion of the elastic element where the air hole is located moves close to the end portion, the air hole is contracted, the air hole and the air flow through hole are blocked up against each other so as to allow the elastic element to be in the second state.

Further, when the movable end of the elastic element moves away from the side wall of the end portion, the air flow through hole is exposed to communicate with the air inlet channel so as to allow the elastic element to be in the first state; when the movable end of the elastic element moves close to the side wall of the end portion until the movable end is adhered to the side wall of the end portion, the air flow through hole is shielded and the air inlet channel is blocked so as to allow the elastic element to be in the second state.

The present application also provides an atomizer which includes any one of the aforementioned atomizing heads.

Further, the atomizer further includes a top cover, an outer support frame, a glass sleeve, a vent pipe, and an atomizer base with a vent, the glass sleeve is sleeved in the outer support frame; the top cover is fixed on an upper end of the outer support frame; the atomizer base is provided on a lower end of the outer support frame; a lower end of the atomizer is fixed on the atomizer base; the vent is in communication with the air inlet channel, an upper end of the atomizing head is connected with a lower end of the vent pipe in a sleeved manner; and an upper end of the vent pipe is fixedly connected with a lower end of the top cover.

Further, an air regulating ring is provided on a periphery of the atomizer base; an air regulating hole is provided on the air regulating ring, where a communication area between the air regulating hole and the vent can be adjusted by adjusting relative positions of the air regulating ring and the atomizer base.

According to another aspect of the present application, an electronic cigarette is also provided, where the electronic cigarette includes any one of the atomizers described above.

Compared with the prior art, the atomizing head of the present application includes a shell provided with a liquid inlet and an inner cavity; and an atomizing head base provided with an air inlet channel. The liquid inlet and the air inlet channel both communicate with the inner cavity. A bottom end of the shell is fixedly connected to the atomizing head base, and an elastic element encloses an air outlet end of the air inlet channel. The elastic element has a first state in which the air inlet channel is in communication with the inner cavity; the elastic element also has a second state in which the air inlet channel and the inner cavity are blocked up against each other. Due to the elastic element, when the atomizing head is used, the communication between the air inlet channel and the inner cavity can be enabled or disabled as required; when the atomizing head is in a non-use state, the air inlet channel and the inner cavity are blocked up against each other, thereby effectively avoiding the problem of leakage of tobacco liquid through the inner cavity from the air inlet channel.

The preferred solutions of the present application and their beneficial effects will be further described in detail with reference to specific embodiments.

BRIEF DESCRIPTION OF DRAWINGS

The accompanying drawings are used to provide a further understanding of the present application, constitute a part of the specification, and are used to explain the present application together with the following specific embodiments, but should not be construed as limiting the present application. In the drawings.

| Part Number Form | | | |
|---|---|---|---|
| Atomizing head | 1 | Mouthpiece | 21 |
| Atomizing head upper cover | 11 | Tobacco channel | 211 |
| Shell | 12 | Top cover | 31 |
| Liquid inlet | 121 | Liquid storage cavity | 41 |
| Liquid absorbing element | 13 | Glass sleeve | 51 |
| Heating element | 14 | Outer support frame | 61 |
| Atomizing head base | 15 | Air regulating ring | 71 |
| Elastic element | 16 | Air regulating hole | 711 |
| Inner cavity | 17 | Atomizer base | 81 |
| Clamp | 161 | Vent | 811 |
| Air inlet channel | 151 | Connecting collar | 92 |
| End portion | 153 | Base connecting ring | 91 |
| Main portion | 154 | Sealing ring | 111 |
| Air inlet portion | 156 | Vent pipe | 101 |
| Gap groove | 155 | Atomizer | 100 |

| Part Number Form | | | |
|---|---|---|---|
| Air flow hole | 152 | Switch | 201 |
| Battery | 200 | | |

DESCRIPTION OF EMBODIMENTS

The specific embodiments of the present application will be described in detail below with reference to the accompanying drawings. It should be understood that the specific embodiments described herein are only used to illustrate and explain the present application and are not intended to limit the present application.

Figure 1:
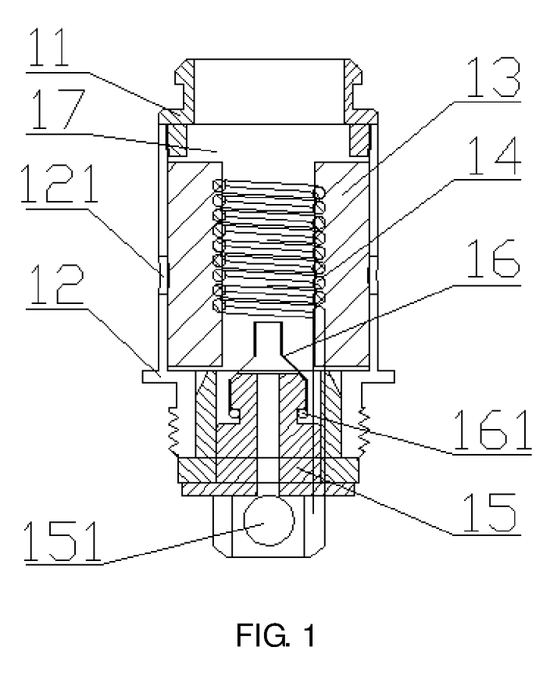
FIG. 1 is a section view of a use state of an atomizing head according to a first embodiment of the present application.
Figure 2:
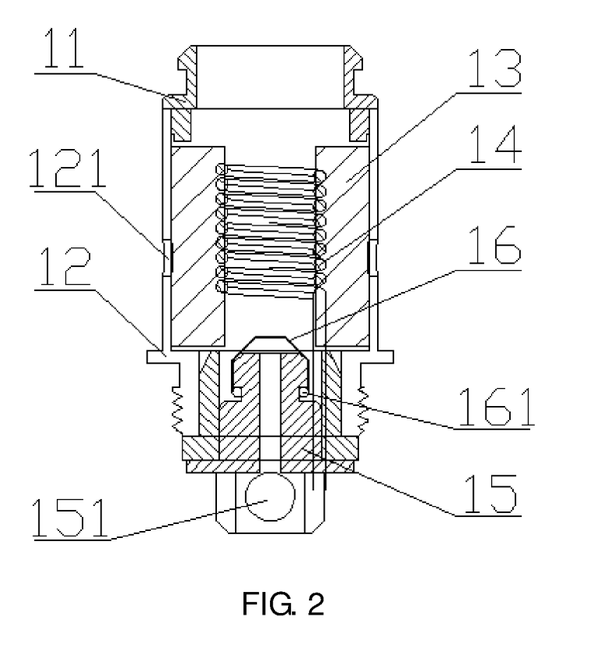
FIG. 2 is a section view of a non-use state of the atomizing head shown in FIG. 1.

Referring to FIG. 1 and FIG. 2, which show the section views of the atomizing head 1 according to the first embodiment of the present application in a use state and a non-use state. The atomizing head 1 in the first embodiment of the present application includes a liquid absorbing element 13 and a heating element 14. The liquid absorbing element 13 may be one or a combination of cotton, a cotton cloth, a glass fiber rope, a porous ceramic, a foam metal, or a foam graphite, and the heating element 14 may be a heating wire, a heating sheet, or a heating plate and the like, which is not limited here. The liquid absorbing element 13 is configured to suck tobacco liquid from the outside and store it. When the heating element 14 is energized, the liquid tobacco stored in the liquid absorbing element 13 is heated and atomized. When the liquid tobacco is consumed and the liquid absorbing element 13 itself is not saturated, the liquid absorbing element 13 can suck tobacco liquid again from the outside to complete the replenishment process. The atomizing head 1 further includes an atomizing head upper cover 11, a shell 12 with a liquid inlet 121 and an inner cavity 17, the liquid inlet 121 communicates with the inner cavity 17, and the liquid absorbing element 13 and the heating element 14 are both provided in the inner cavity 17 of the shell 12. The atomizing head 1 further includes an atomizing head base 15 provided with an air inlet channel 151. A bottom end of the shell 12 is fixedly connected with the atomizing head base 15, and the air inlet channel 151 is also connected with the inner cavity 17. An elastic element 16 encloses an air outlet end of the air inlet channel 151. The elastic element 16 has a first state in which it communicates the air inlet channel 151. Referring to FIG. 1 for the first state. The plastic part further includes a second state in which it blocks up the air inlet channel 151. In the second state, referring to FIG. 2. When the atomizing head 1 is in a non-use state, the elastic element 16 will restore its initial state. In this embodiment, the atomizing head upper cover 11 and the shell 12 are two independent structures. In fact, the atomizing head upper cover 11 and the shell 12 can be integrated into one body, so as to save time and facilitate assembly. It should be pointed out that the upper portion of the atomizing head upper cover 11 is not a closed structure but an open design so as to make the tobacco flow out easily.

Figure 3:
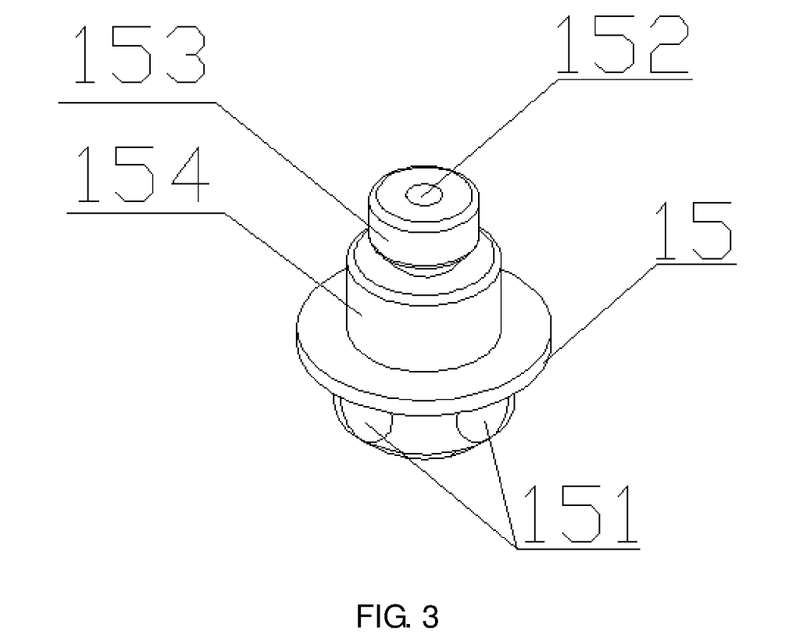
FIG. 3 is a perspective view of a first embodiment of the atomizing head base according to the present application.
Figure 4:
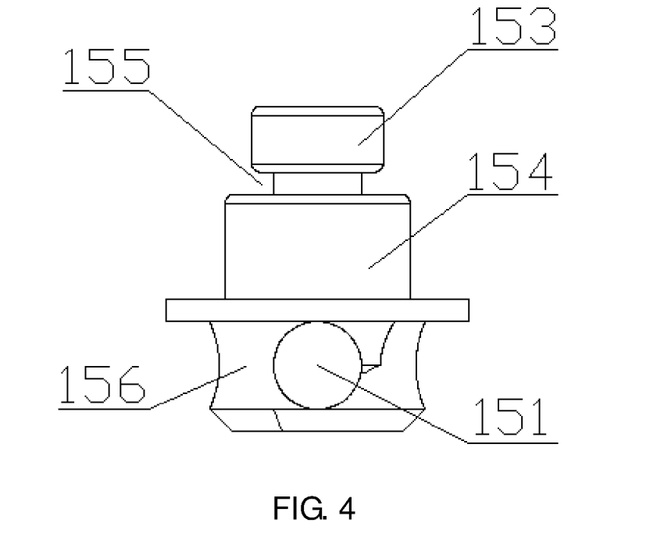
FIG. 4 is a front view of the atomizing head base shown in FIG. 3.

In order to better explain the working principle of the atomizing head 1 of the present embodiment, please refer to the atomizing head base 15 shown in FIG. 3 and FIG. 4 which is applied to the atomizing head 1 of the first embodiment. The atomizing head base 15 includes an end portion 153, a main portion 154, and an air inlet portion 156, which are arranged in turn from top to bottom. The main portion 154 is provided between the end portion 153 and the air inlet portion 156. A gap groove 155 is provided between the end portion 153 and the main portion 154. The end portion 153 and the main portion 154 are provided in the shell 12. Referring to FIG. 1, according to one preferred implementation of the embodiment, a lower end of the elastic element 16 is fixed in the gap groove 155 with a clamp 161.

An air flow through hole 152 is provided above the end portion 153 of the atomizing head base 15. The air flow through hole 152 serves as an outlet end of the air inlet channel 151, and is operatively in communication with an air hole (unsigned) provided on the elastic element 16. When the elastic element 16 is in the first state, that is, in an extended state under the action of the gas flow, the air hole expands and communicates with the air flow through hole 152. When the elastic element 16 is in the second state, no more gas flow is sucked in. The elastic element 16 maintains the initial state accordingly, the air hole does not expand and thus does not communicate with the air flow through hole 152.

Figure 5:
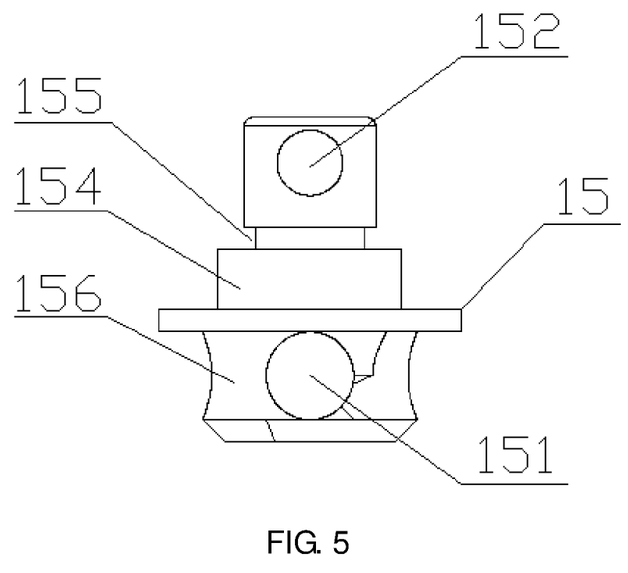
FIG. 5 is a front view of a second embodiment of the atomizing head base according to the present application.
Figure 6:
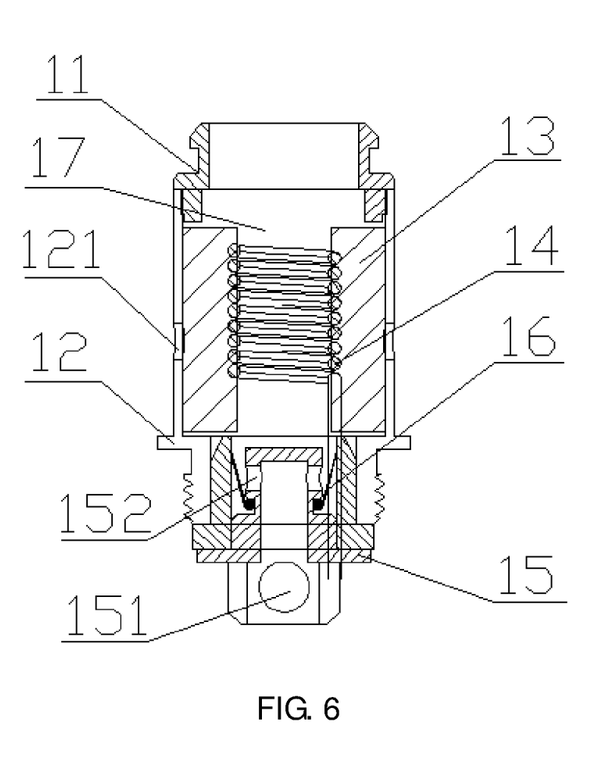
FIG. 6 is a section view of an atomizing head in a use state according to a second embodiment of the present application.
Figure 7:
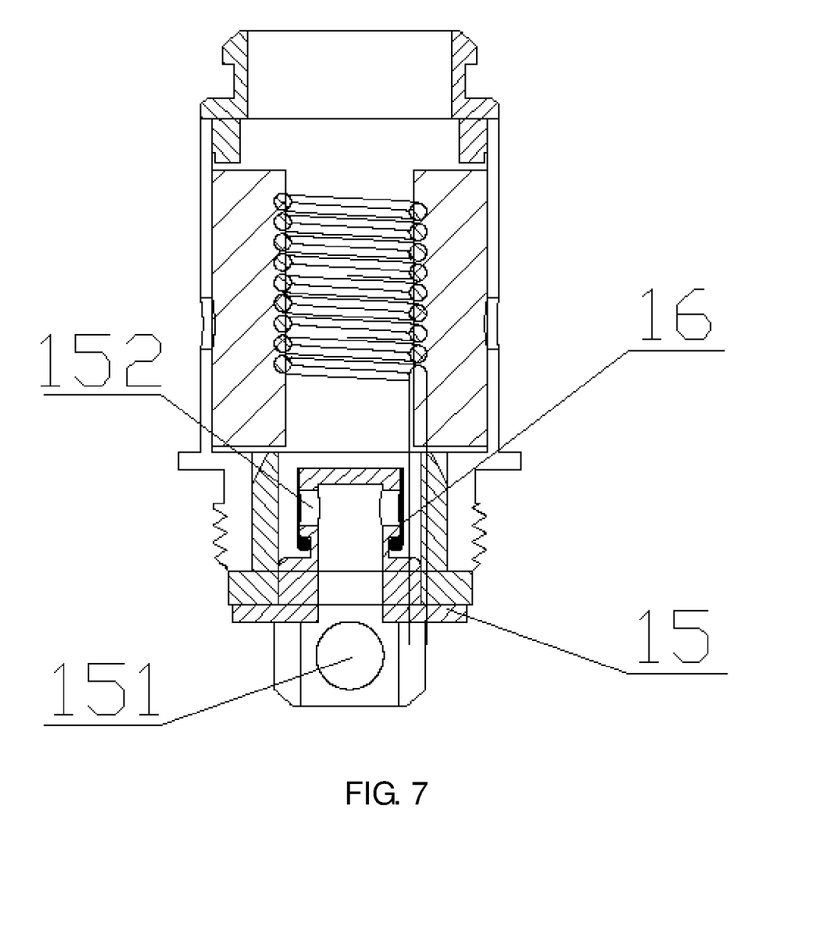
FIG. 7 is a section view of an atomizing head in a non-use state applying a second embodiment of the present application.

FIG. 5 shows an atomizing head base 15 according to the second embodiment of the present application. Different from the atomizing head base 15 shown in the first embodiment, the air flow through hole 152 of the atomizing head base 15 is provided on a side wall of the end portion 153 of the atomizing head base 15. In conjunction with FIG. 6, FIG. 6 shows a section view of the structure of the atomizing head base 15 shown in the first embodiment being installed on the atomizing head 1. In this embodiment, one end of the elastic element 16 is movable, the other end is fixed in the gap groove 155. The elastic element 16 is no longer provided with air holes. When the elastic element 16 is in the first state, that is, under the action of the gas flow, the movable end of the elastic element 16 moves away from the side wall of the end portion 153, and the air flow through hole 152 is exposed to communicate with the air inlet channel 151. When the elastic element 16 is in the second state, as shown in FIG. 7, no more gas flow is sucked in, so the elastic element 16 maintains in the initial state, the elastic element 16 is adhered to the side wall of the end portion 153 under the action of the elastic force, and the air flow through hole 152 is shielded from communicating with the air inlet channel 151.

As can be seen from the structural description of the atomizing head 1 in the above two embodiments, since the elastic element 16 encloses the outlet end of the air inlet channel 151 of the atomizing head base 15, even if the liquid absorbing element 13 exudes part of the tobacco liquid because of excessive saturation, it will not flow out of the atomizing head 1 through the air inlet channel 151, and thereby effectively avoiding the problem of liquid leakage of the atomizing head 1.

Figure 8:
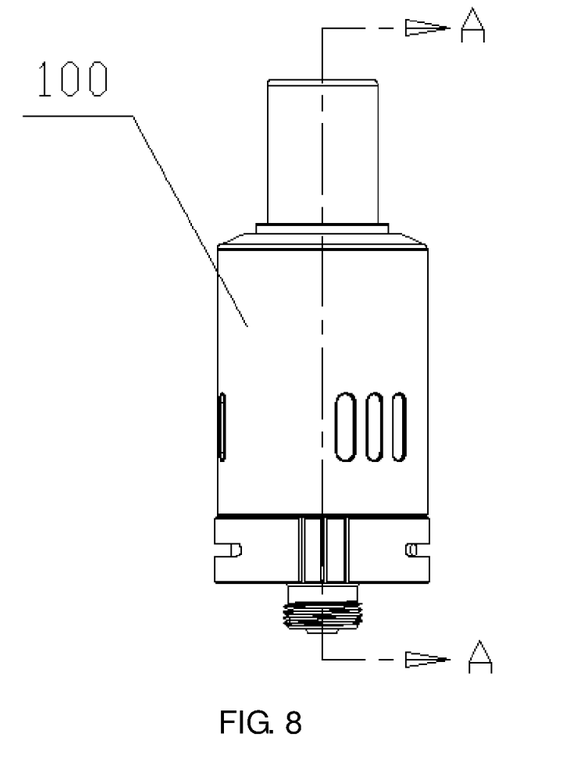
FIG. 8 is a front view of an atomizer applying an atomizing head of the first embodiment of the present application.
Figure 9:
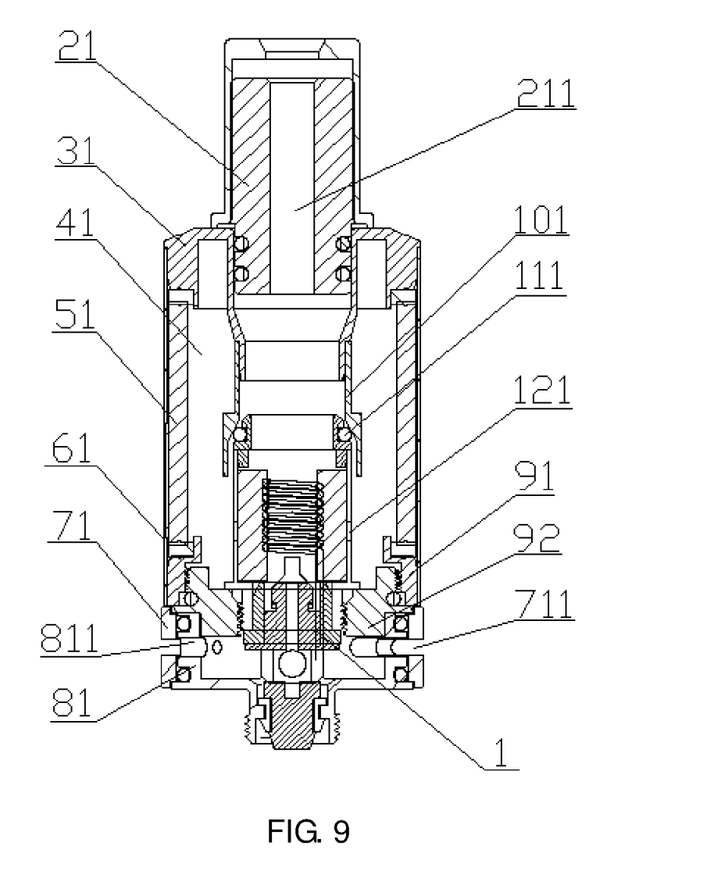
FIG. 9 is a section view along A-A of the atomizer shown in FIG. 8.

Referring to the atomizer 100 applying the foregoing atomizing head 1 shown in FIG. 8 and FIG. 9, the atomizer 100 includes a top cover 31, an outer support frame 61, a glass sleeve 51, a vent pipe 101, and an atomizer base 81 with a vent 811. The glass sleeve 51 is sleeved in the outer support frame 61; the top cover 31 is fixed on an upper end of the outer support frame 61; the atomizer base 81 is provided on a lower end of the outer support frame 61; the atomizing head 1 is provided in an inner cavity of the glass sleeve 51; a lower end of the atomizing head 1 is fixed on the atomizer base 81; the vent 811 is in communication with the air inlet channel 151. The atomizing head 1 may be any one of the atomizing heads described in the foregoing embodiments. An upper end of the atomizing head 1 is connected to a lower end of the vent pipe 101 in a sleeved manner; an upper end of the vent pipe 101 is fixedly connected to a lower end of the top cover 31; an air flow channel formed in an inner cavity of the vent pipe 101 is in communication with an inner cavity of the atomizing head 1. Referring to FIG. 8, the space between the glass sleeve 51 and the vent pipe 101, the shell 12 of the atomizing head 1 is a liquid storage cavity 41. The liquid inlet 121 of the atomizing head 1 is communication with the liquid storage cavity 41 to facilitate the atomizing head 1 to suck the tobacco liquid in the liquid chamber 41 through the liquid inlet 121. In order to prevent the tobacco liquid from entering into the air flow channel, a sealing ring 111 is also provided at the joint of the vent pipe 101 and the atomizing head 1. In this embodiment, when a user uses the atomizer 100, a mouthpiece 21 is inserted into a corresponding position on the top cover 31, so that a tobacco channel 211 provided in an inner cavity of the mouthpiece 21 communicates with the air flow channel, and the user can suck tobacco generated in the atomizing head 1 through the mouthpiece 21. It can be seen from the present embodiment that the air inlet is also located at the lower end of the atomizing head 1, and the liquid inlet 121 is located relatively above. However, due to the elastic element 16 on the atomizing head base 15, even if the liquid absorbing element 13 is excessively saturated by sucking the tobacco liquid, the overflowed tobacco liquid will not leak out from the air inlet channel 151.

An air regulating ring 71 is provided on a periphery of the atomizer base 81. The air regulating ring 71 is provided with an air regulating hole 711 to adjust relative positions of the air regulating ring 71 and the atomizer base 81, as well as a communication area between the air regulating hole 711 and the vent 811, thereby adjusting the amount of air entering the atomizer 100, thus adjusting the amount of tobacco to be generated. As one of the preferred implementations of the present embodiment, the air regulating ring 71 is provided on the periphery of the atomizer base 81 in a rotatable manner, thus rendering it convenient for user operation. The atomizer base 81 also includes a connecting collar 92 that is fixedly connected to an upper end of the atomizer base 81. Both of the inner and outer walls of the connecting collar 92 are provided with threads. The threads on the outer wall of the connecting collar 92 are screwed to the outer support frame 61, and the threads on the inner wall of the connecting collar 92 are screwed to the atomizing head base 81. Further, according to another implementation of the present embodiment, a base connecting ring 91 is further provided at the lower end of the outer support frame 61. The base connecting ring 91 may be fastened to the lower end of the outer support frame 61 by a thread or in a manner of interference fit. Threads may be provided at an inner peripheral side of the base connecting ring 91 for being screwed to the threads on the outer wall of the connecting collar 92.

Figure 10:
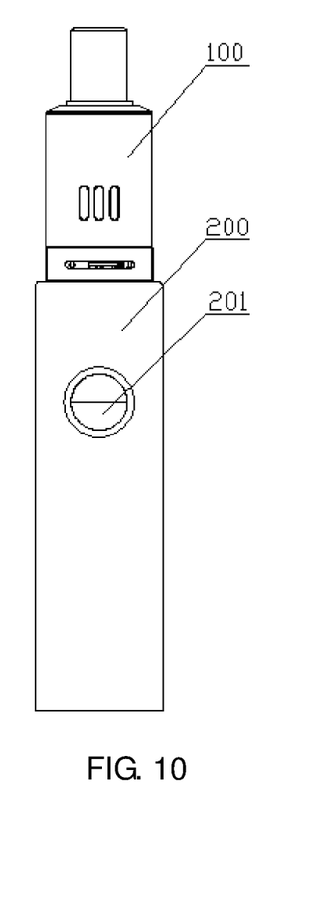
FIG. 10 is a front view of an electronic cigarette according to the present application.

According to another aspect of the present application, an electronic cigarette is also provided. Referring to an electronic cigarette shown in FIG. 10, the electronic cigarette applies the atomizer 100 according to any one of the foregoing embodiments. The atomizer 100 is provided above the battery 200. A switch 201 is provided outside the battery 200, the switch 201 can control an on or off state of the circuit in the atomizer 100 or adjust the amount of tobacco. It can be understood that the switch 201 may also be arranged above the atomizer 100. Due to the technical effect of the leakage preventing effect that the atomizer 100 can achieve, the electronic cigarette to which the aforesaid atomizer 100 is applied should also have the same technical effect.

Any combination of various embodiments of the present application as long as it does not violate the concept of the present application shall be regarded as the content of the present disclosure; within the scope of the technical idea of the present application, various simple variants of the technical solution and any combination of different embodiments without departing from the concept of the application should fall within the protection scope of the present application.

What is claimed is:

1. An atomizing head, wherein the atomizing head comprises a shell provided with a liquid inlet and an inner cavity, and an atomizing head base provided with an air inlet channel, wherein the liquid inlet and the air inlet channel are both in communication with the inner cavity; a bottom end of the shell is fixedly connected to the atomizing head base;

an elastic element encloses an air outlet end of the air inlet channel; the elastic element has a first state in which the air inlet channel is in communication with the inner cavity, and the elastic element also has a second state in which the air inlet channel and the inner cavity are blocked from each other.

2. The atomizing head according to claim 1, wherein the atomizing head base comprises an end portion, a main portion and an air inlet portion, which are arranged in turn from top to bottom; the main portion is provided between the end portion and the air inlet portion, a gap groove is provided between the end portion and the main portion, the end portion and the main portion are provided within the inner cavity, and an end portion of the elastic element is fixed in the gap groove.

3. The atomizing head according to claim 2, wherein the elastic element is provided with an air hole, an air flow through hole serving as the air outlet end of the air inlet channel is provided above the end portion, and the elastic element encloses a periphery of the end portion.

4. The atomizing head according to claim 2, wherein a side wall of the end portion is provided with an air flow through hole serving as the air outlet end of the air inlet channel, and the elastic element is adhered to the side wall of the end portion, one end of the elastic element which is movable is a movable end, and the other end of the elastic element is fixed in the gap groove.

5. The atomizing head according to claim 3, wherein when a portion of the elastic element where the air hole is located moves away from the end portion, the air hole is expanded, and the air hole communicates with the air flow through hole so as to allow the elastic element to be in the first state; when the portion of the elastic element where the air hole is located moves close to the end portion, the air hole is contracted, the air hole and the air flow through hole are blocked from each other so as to allow the elastic element to be in the second state.

6. The atomizing head according to claim 4, wherein when the movable end of the elastic element moves away from the side wall of the end portion, the air flow through hole is exposed to communicate with the air inlet channel so as to allow the elastic element to be in the first state; when the movable end of the elastic element moves close to the side wall of the end portion until the movable end is adhered to the side wall of the end portion, the air flow through hole is shielded and the air inlet channel is blocked so as to allow the elastic element to be in the second state.

7. An atomizer, wherein the atomizer comprises the atomizing head according to claim 1.

8. The atomizer according to claim 7, wherein the atomizer further comprises a top cover, an outer support frame, a glass sleeve, a vent pipe, and an atomizer base with a vent, the glass sleeve is sleeved in the outer support frame; the top cover is fixed on an upper end of the outer support frame; the atomizer base is provided on a lower end of the outer support frame; a lower end of the atomizer is fixed on the atomizer base; the vent is in communication with the air inlet channel, an upper end of the atomizing head is connected with a lower end of the vent pipe in a sleeved manner; and an upper end of the vent pipe is fixedly connected with a lower end of the top cover.

9. The atomizer according to claim 8, wherein an air regulating ring is provided on a periphery of the atomizer base; an air regulating hole is provided on the air regulating ring, wherein a communication area between the air regulating hole and the vent can be adjusted by adjusting relative positions of the air regulating ring and the atomizer base.

10. An electronic cigarette, wherein the electronic cigarette comprises the atomizer according to claim 7.

* * * * *